(12) United States Patent
Bellows et al.

(10) Patent No.: US 11,660,161 B2
(45) Date of Patent: May 30, 2023

(54) MEDICAL DEVICE SUSPENSION SYSTEM HAVING CABLE MANAGEMENT ASSEMBLY

(71) Applicant: American Sterilizer Company, Mentor, OH (US)

(72) Inventors: Lance Clark Bellows, Painesville, OH (US); Bernard John Moss, Perry, OH (US); Michael Joseph Heser, Willoughby, OH (US)

(73) Assignee: American Sterilizer Company, Mentor, OH (US)

( * ) Notice: Subject to any disclaimer, the term of this patent is extended or adjusted under 35 U.S.C. 154(b) by 635 days.

(21) Appl. No.: 16/832,571

(22) Filed: Mar. 27, 2020

(65) Prior Publication Data

US 2020/0306006 A1 Oct. 1, 2020

Related U.S. Application Data

(60) Provisional application No. 62/825,078, filed on Mar. 28, 2019.

(51) Int. Cl.
*A61B 90/50* (2016.01)
*A61B 50/28* (2016.01)
(Continued)

(52) U.S. Cl.
CPC .............. *A61B 90/50* (2016.02); *A61B 50/28* (2016.02); *A61B 90/35* (2016.02);
(Continued)

(58) Field of Classification Search
CPC ......... F21W 2131/205; F16M 11/2014; F16M 13/027; A61G 12/004; F21V 23/002;
(Continued)

(56) References Cited

U.S. PATENT DOCUMENTS 3,240,925 A  3/1966 Paschke et al.
3,556,455 A * 1/1971 Storm .................. A61G 12/004
                                          137/355.16
(Continued)

FOREIGN PATENT DOCUMENTS

EP  0300316 A1  1/1989
WO  0145627 A1  6/2001
(Continued)

OTHER PUBLICATIONS

PCT/US2020/025286; PCT International Search Report and Written Opinion of the International Searching Authority dated Jul. 3, 2020.
(Continued)

*Primary Examiner* — Bradley Duckworth
(74) *Attorney, Agent, or Firm* — Renner, Otto, Boisselle & Sklar, LLP

(57) ABSTRACT

A medical device suspension system includes a spindle extending along a longitudinal axis and a cable management cover surrounding the spindle. A gap is formed between the cable management cover and the spindle. A hub is rotatably mounted to the spindle and includes a housing. A top hub cover is disposed along the longitudinal axis between the hub and the cable management cover and defines an end of the gap, the top hub cover including a passage in fluid communication with an internal volume of the housing. The top hub cover is rotatable with respect to the spindle about the longitudinal axis. A cable is provided within the gap, the cable entering the gap at a fixed location about the longitudinal axis and passing into the housing through the passage. Rotation of the top hub cover about the longitudinal axis causes the passage to rotate about the longitudinal axis.

20 Claims, 11 Drawing Sheets

(51) Int. Cl.
*F16M 13/02* (2006.01)
*A61B 90/35* (2016.01)
*F16M 11/20* (2006.01)

(52) U.S. Cl.
CPC ...... *F16M 11/2014* (2013.01); *F16M 13/027* (2013.01); *A61B 2505/01* (2013.01); *A61B 2505/05* (2013.01)

(58) Field of Classification Search
CPC ......... F21V 21/26; A61B 90/50; A61B 50/28; A61B 90/35
See application file for complete search history.

(56) References Cited

U.S. PATENT DOCUMENTS

| | | | |
|---|---|---|---|
| 4,901,339 A | 2/1990 | Heinz et al. | |
| 5,808,680 A * | 9/1998 | Steckhan | H04N 7/18 348/370 |
| 6,095,468 A | 8/2000 | Chirico et al. | |
| 6,454,116 B1 | 9/2002 | O'Neill | |
| 6,471,363 B2 | 10/2002 | Howell et al. | |
| 6,619,606 B2 | 9/2003 | Oddsen, Jr. et al. | |
| 6,633,328 B1 | 10/2003 | Byrd et al. | |
| 6,639,623 B2 | 10/2003 | Howell et al. | |
| 6,899,307 B2 | 5/2005 | Strauss et al. | |
| 6,899,442 B2 | 5/2005 | Howell et al. | |
| 7,065,811 B2 * | 6/2006 | Newkirk | F16M 11/26 5/658 |
| 7,097,145 B2 | 8/2006 | Turner | |
| 7,219,864 B2 | 5/2007 | Strauss et al. | |
| 7,593,217 B2 | 9/2009 | Shahrokhi | |
| 7,726,823 B2 | 6/2010 | Rus et al. | |
| 8,070,331 B2 | 12/2011 | Gull et al. | |
| 8,154,859 B2 | 4/2012 | Shahrokhi | |
| 8,424,833 B2 | 4/2013 | Muller et al. | |
| 9,022,339 B2 | 5/2015 | Borg et al. | |
| 9,239,127 B2 | 1/2016 | Kronung | |
| 2001/0030683 A1 | 10/2001 | Howell et al. | |
| 2004/0020675 A1 * | 2/2004 | Bally | A61G 12/004 174/50 |
| 2005/0242261 A1 | 11/2005 | Brahler et al. | |
| 2006/0102811 A1 | 5/2006 | Musset et al. | |
| 2007/0012853 A1 | 1/2007 | Strauss et al. | |
| 2014/0131526 A1 | 5/2014 | Borg et al. | |
| 2017/0222419 A1 | 8/2017 | Oginski et al. | |
| 2017/0290725 A1 | 10/2017 | Oginski et al. | |
| 2020/0268476 A1 * | 8/2020 | Bellows | A61G 12/004 |

FOREIGN PATENT DOCUMENTS

| | | |
|---|---|---|
| WO | 03025453 A1 | 3/2003 |
| WO | 03040609 A1 | 5/2003 |
| WO | 2008112675 A1 | 9/2008 |
| WO | 2011060846 A1 | 5/2011 |

OTHER PUBLICATIONS

International Preliminary Report on Patentability for related International Application No. PCT/US2020/025286 dated Oct. 7, 2021.

* cited by examiner

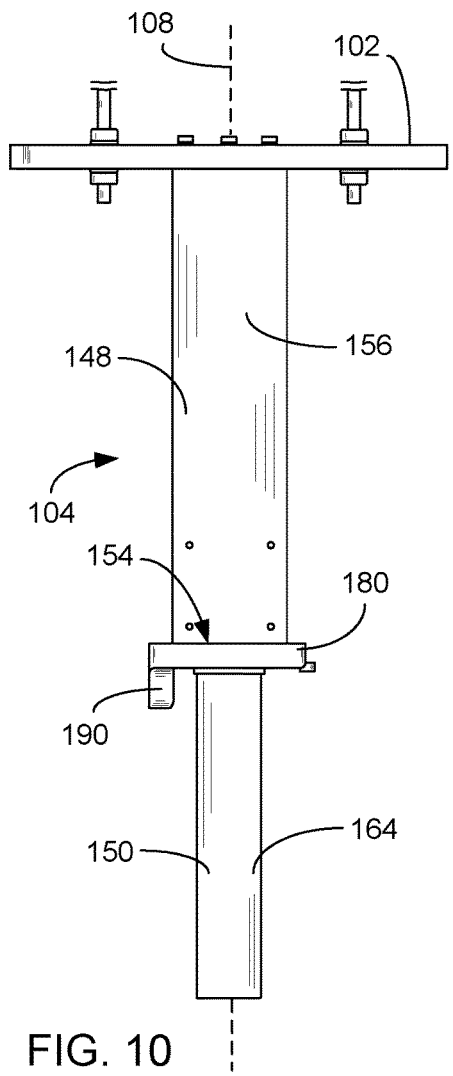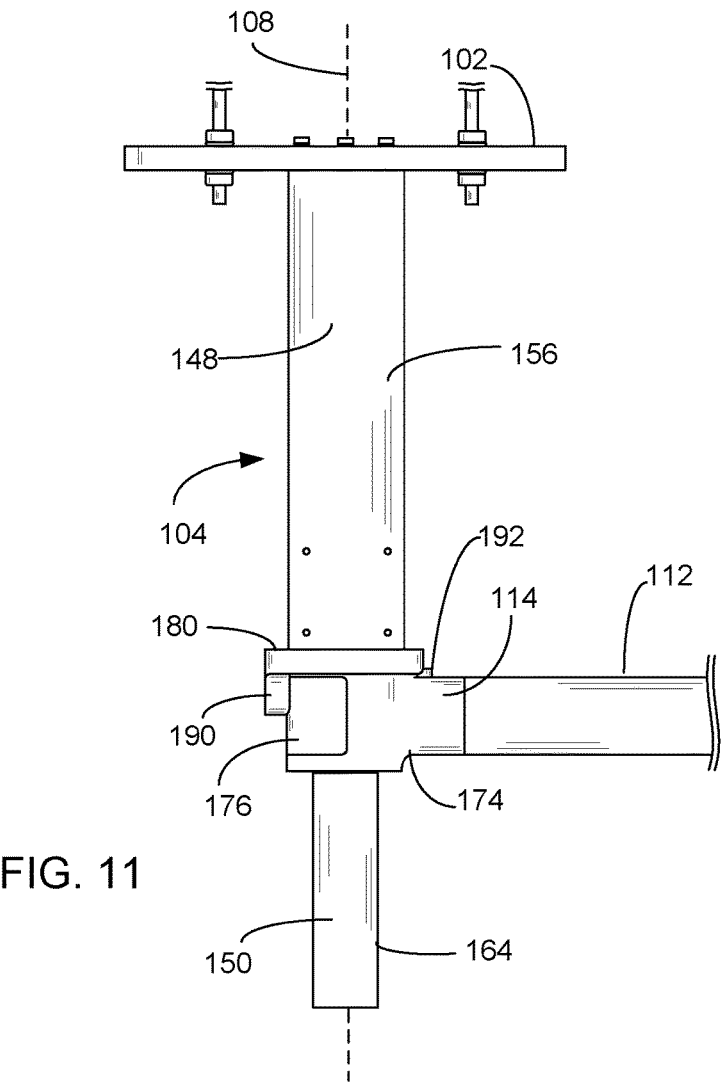
FIG. 10
FIG. 11

MEDICAL DEVICE SUSPENSION SYSTEM HAVING CABLE MANAGEMENT ASSEMBLY

This application claims the benefit of U.S. Provisional Patent Application No. 62/825,078, filed Mar. 28, 2019, the disclosure of which is incorporated herein by reference in its entirety.

FIELD OF INVENTION

This application relates generally to a medical device suspension system for use in, for example, a hospital examination room, a clinic, a surgery room or an emergency room; and more particularly to a medical device suspension system having a cable management assembly for routing cable to a medical device or component mounted to an extension arm of the medical device suspension system.

BACKGROUND

Medical device suspension systems are used in health treatment settings such as hospital examination rooms, clinics, surgery rooms and emergency rooms. These systems may be mounted to a structure (e.g., a structural plate at the ceiling or wall), and may suspend or support any variety of medical devices or components including surgical lights, supply consoles, patient monitors, camera detector heads, medical instruments, ventilator systems, suction devices, among others.

Many of the medical devices or components that are supported by the extension arms require a hardwired connection (e.g., electrical, network, etc.), which necessitates the running of one or more cables to the medical devices or components. Routing these cables within the medical device suspension system is a desired approach, as externally routed cables may become tangled and/or damaged as the medical device suspension system is used. Internally routed cables are also preferred from the standpoint of aesthetics. However, pressure to reduce the size and profile of the medical device suspension system while maintaining the functionality (e.g., rotatability) of the extension arms, particularly the extension arm(s) located closest to the structure to which the medical device suspension system is mounted, has presented limitations of the ability to internally route cables in the medical device suspension system. The limited space/length provided to route such cables to the top/upper arms results in the inability to route the cable in a manner that allows for the cable to sufficiently move/flex with movement of the arm, and/or results in increased fatigue on the cables when the medical device suspension system is in use. As a result, many conventional medical device suspension system designs including internal cable routing restrict the location of accessories requiring cable routing to the lower arm(s) (through the interior of the spindle and to the lower arm). Other conventional medical device suspension system designs that attempt to provide internal cable routing to the supported medical devices or components require the use of specific cable coupling and harness arrangements that still may restrict the ability of particular medical devices or components to be mounted on the upper arm(s) due to limitations on the size and/or type of cable that can be routed using this specific design.

SUMMARY OF INVENTION

The present disclosure relates to a medical device suspension system having a cable management assembly for routing cable to a medical device or component mounted to an extension arm of the medical device suspension system.

In accordance with one aspect of the present disclosure, a medical device suspension system includes: a spindle having an outer major surface and extending along a longitudinal axis; a cable management cover surrounding the spindle about the longitudinal axis and having an inner major surface, the cable management cover extending along the longitudinal axis between a first end and a second end such that a gap is formed between the inner major surface of the cable management cover and a portion of the outer major surface of the spindle; a hub rotatably mounted to the spindle, the hub including a hub housing; a top hub cover disposed along the longitudinal axis between the hub and the cable management cover, the top hub cover defining an end of the gap formed between the inner major surface of the cable management cover and the outer major surface of the spindle along the longitudinal axis, the top hub cover including a passage in fluid communication with an internal volume of the hub housing, the top hub cover rotatable with respect to the spindle about the longitudinal axis; and a cable provided within the gap, the cable entering the gap proximate the first end of the cable management cover at a fixed location about the longitudinal axis, the cable passing into the hub housing through the passage of the top hub cover, wherein rotation of the top hub cover about the longitudinal axis causes the position of the passage to rotate about the longitudinal axis, while the position at which the cable enters the gap about the longitudinal axis remains stationary.

In some embodiments, the medical device suspension system further includes a mounting plate, wherein the spindle is mounted to the mounting plate. In some embodiments, the mounting plate includes cable routing orifice in fluid communication with the gap. In some embodiments, the cable management cover is mounted to the mounting plate and the top hub cover is rotatable with respect to the cable management cover about the longitudinal axis In some embodiments, the spindle includes a drop tube portion and a hub mounting portion; the drop tube portion extends along the longitudinal axis between a first end and a second end; the hub mounting portion extends along the longitudinal axis between a first end and a second end; the first end of the hub mounting portion is mounted to the drop tube portion proximate the second end of the drop tube portion; and the hub is mounted to the hub mounting portion.

In some embodiments, the length of the drop tube portion along the longitudinal axis is 125 mm to 675 mm.

In some embodiments, the length of the drop tube portion along the longitudinal axis is 150 mm to 330 mm.

In some embodiments, the gap is an annular gap, and the cable is wrapped at least 180° around the spindle.

In some embodiments, the gap is an annular gap, and the cable is wrapped at least 360° around the spindle.

In some embodiments, the medical device suspension system further includes an additional hub rotatably mounted to the spindle, the additional hub located further from the top hub cover along the longitudinal axis than the hub.

In some embodiments, the gap between the inner major surface of the cable management cover and the portion of the outer major surface of the spindle is 100 mm or less.

In some embodiments, the top hub cover includes: a first major surface and a second major surface opposite the first major surface and spaced apart from the first major surface along the longitudinal axis; a side wall extending from the first major surface in a direction parallel to the longitudinal axis; and a recessed portion of the major surfaces that is offset relative to the remainder of the major surfaces along the longitudinal axis, the recessed portion constituting the passage in fluid communication the internal volume of the hub housing.

In accordance with another aspect of the present disclosure, a medical device suspension system includes: a mounting plate including a cable routing orifice; a spindle mounted to the mounting plate, the spindle having an outer major surface and extending along a longitudinal axis; a cable management cover surrounding the spindle about the longitudinal axis and having an inner major surface, the cable management cover extending along the longitudinal axis between a first end and a second end such that a gap is formed between the inner major surface of the cable management cover and a portion of the outer major surface of the spindle, the cable routing orifice in fluid communication with the gap; a hub rotatably mounted to the spindle, the hub including a hub housing; and a top hub cover disposed along the longitudinal axis between the hub and the cable management cover, the hub cover defining an end of the gap formed between an inner major surface of the cable management cover and an outer major surface of the spindle along the longitudinal axis, the top hub cover including a passage in fluid communication with an internal volume of the hub housing, the top hub cover rotatable with respect to the spindle about the longitudinal axis wherein rotation of the top hub cover about the longitudinal axis causes the position of the passage to rotate about the longitudinal axis, while the position at which the cable enters the gap about the longitudinal axis remains stationary.

In some embodiments, the cable management cover is mounted to the mounting plate and the top hub cover is rotatable with respect to the cable management cover about the longitudinal axis In some embodiments, the spindle includes a drop tube portion and a hub mounting portion; the drop tube portion extends along the longitudinal axis between a first end and a second end; the hub mounting portion extends along the longitudinal axis between a first end and a second end; the first end of the hub mounting portion is mounted to the drop tube portion proximate the second end of the drop tube portion; and the hub is mounted to the hub mounting portion.

In some embodiments, the length of the drop tube portion along the longitudinal axis is 125 mm to 675 mm.

In some embodiments, the length of the drop tube portion along the longitudinal axis is 150 mm to 330 mm.

In some embodiments, the medical device suspension system further includes an additional hub rotatably mounted to the spindle, the additional hub located from the top hub cover along the longitudinal axis than the hub.

In some embodiments, the gap between the inner major surface of the cable management cover and the portion of the outer major surface of the spindle is less than 100 mm.

In some embodiments, the top hub cover includes: a first major surface and a second major surface opposite the first major surface and spaced apart from the first major surface along the longitudinal axis; a side wall extending from the first major surface in a direction parallel to the longitudinal axis; and a recessed portion of the major surfaces that is offset relative to the remainder of the major surfaces along the longitudinal axis, the recessed portion constituting the passage in fluid communication the internal volume of the hub housing.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the present disclosure.

FIG. 10 is a schematic side view of parts of an exemplary medical device suspension system in accordance with an embodiment of the present disclosure.

FIG. 11 is a schematic side view of parts of an exemplary medical device suspension system in accordance with an embodiment of the present disclosure.

DETAILED DESCRIPTION

Figure 1:
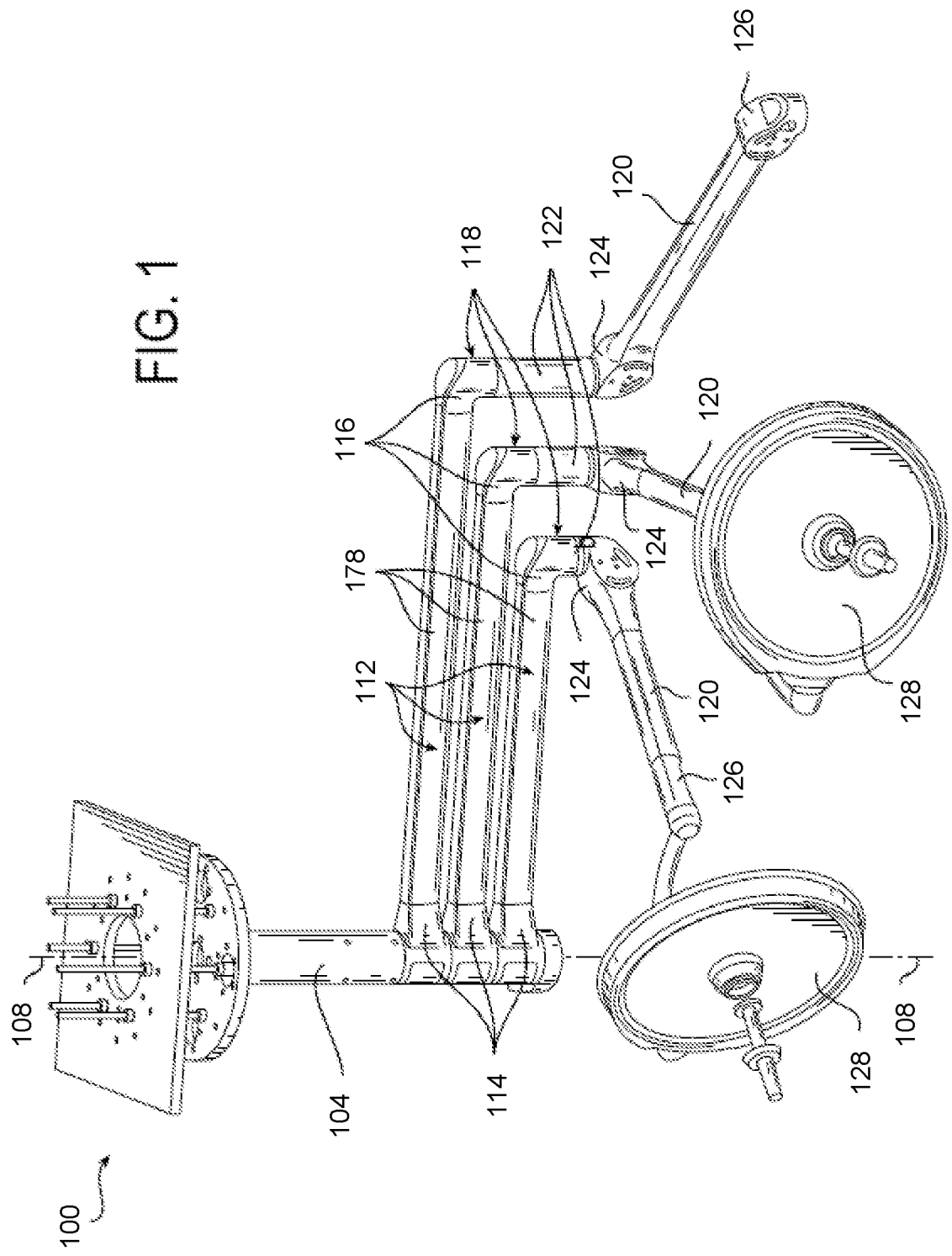
FIG. 1 is a schematic perspective view of an exemplary medical device suspension system in accordance with an embodiment of the present disclosure.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. Any alterations and further modifications of the described embodiments, and any further applications of the principles of the present disclosure as described herein, are contemplated as would normally occur to one skilled in the art to which the present disclosure relates.

Figure 2:
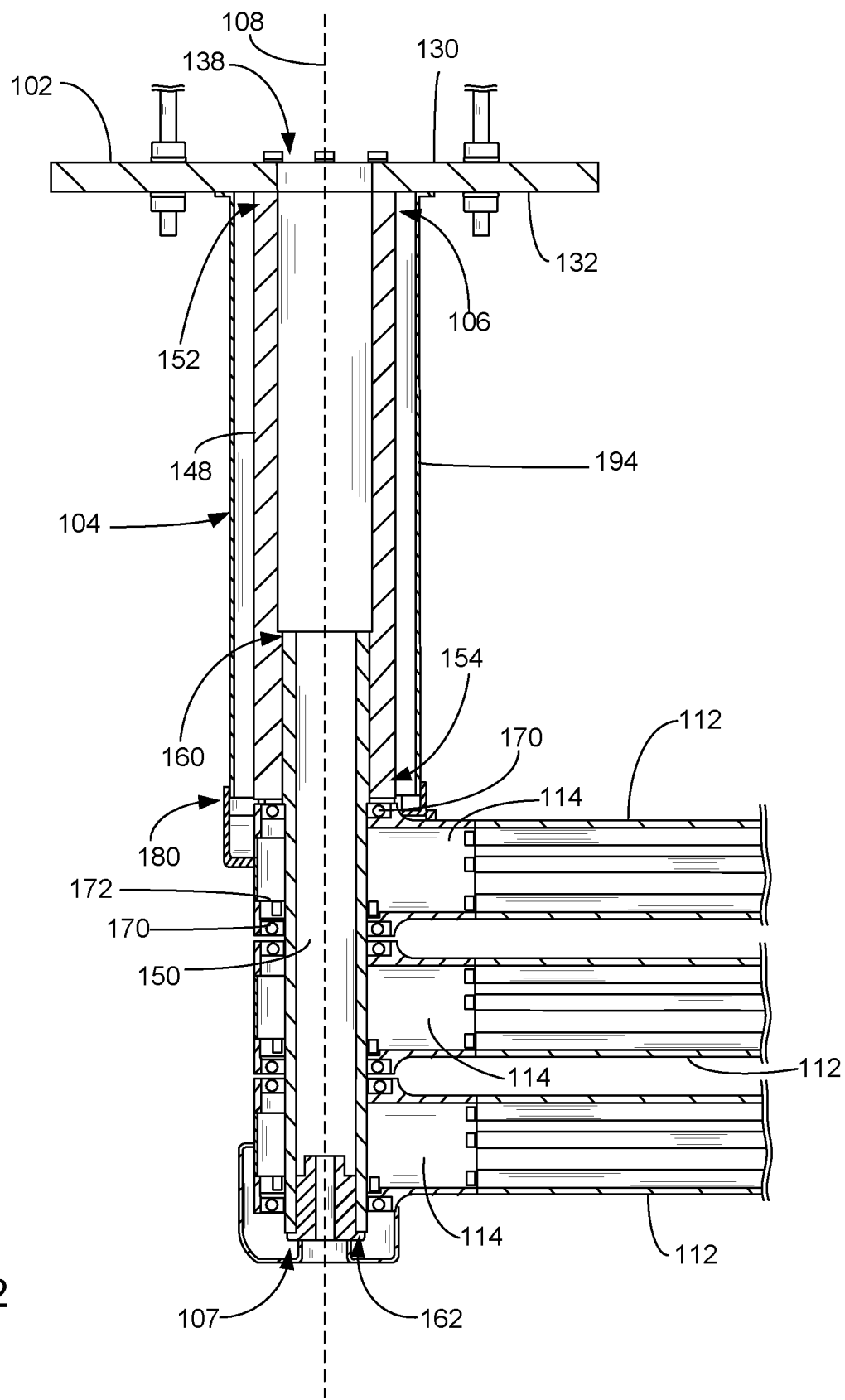
FIG. 2 is a schematic cross-sectional view of parts of an exemplary medical device suspension system in accordance with an embodiment of the present disclosure.

With initial reference to FIGS. 1 and 2, an exemplary medical device suspension system having a cable management assembly is shown at 100. The medical device suspension system 100 includes a primary (e.g., central) spindle 104 that is suspended from a mounting plate 102. A proximal end 106 of the spindle 104 is mounted to the mounting plate 102, and the spindle 104 extends along a longitudinal axis 108 to a distal end 107 of the spindle 104. The mounting plate 102 may be mounted to a structural plate 110, which may be provided as part of a building structure (e.g., at the ceiling or wall). In the example shown, three extension arms 112 are respectively mounted to the spindle 104 for rotational movement about the spindle via hubs 114 at the proximal ends the extension arms. The extension arms 112 each include at their distal end 116 (distal the hub 114 and spindle 104) a knuckle joint assembly 118. Load balancing arms 120, which are also referred to as counterbalancing arms, are respectively mounted to the extension arms via the knuckle joint assembly 118. The knuckle joint assembly 118 may rotatably support a spindle 122 of a respective load balancing arm 120 at a proximal end 124 of the load balancing arm 120. The distal end 126 of each load balancing arm 120 is configured with a suitable support hub to support a medical device 128. The medical device 128 may include a surgical light as shown, or a supply console, a patient monitor, a camera detector head, a medical instrument, a ventilator system, a suction device, among others. While the example shown in FIGS. 1 and 2 include three extension arms 112 and load balancing arms 120, it will be appreciated that in other embodiments, the medical device suspension system may include fewer (e.g., 1, 2) or more (e.g., 4, 5, etc.) extension arms than is shown.

Figure 3:
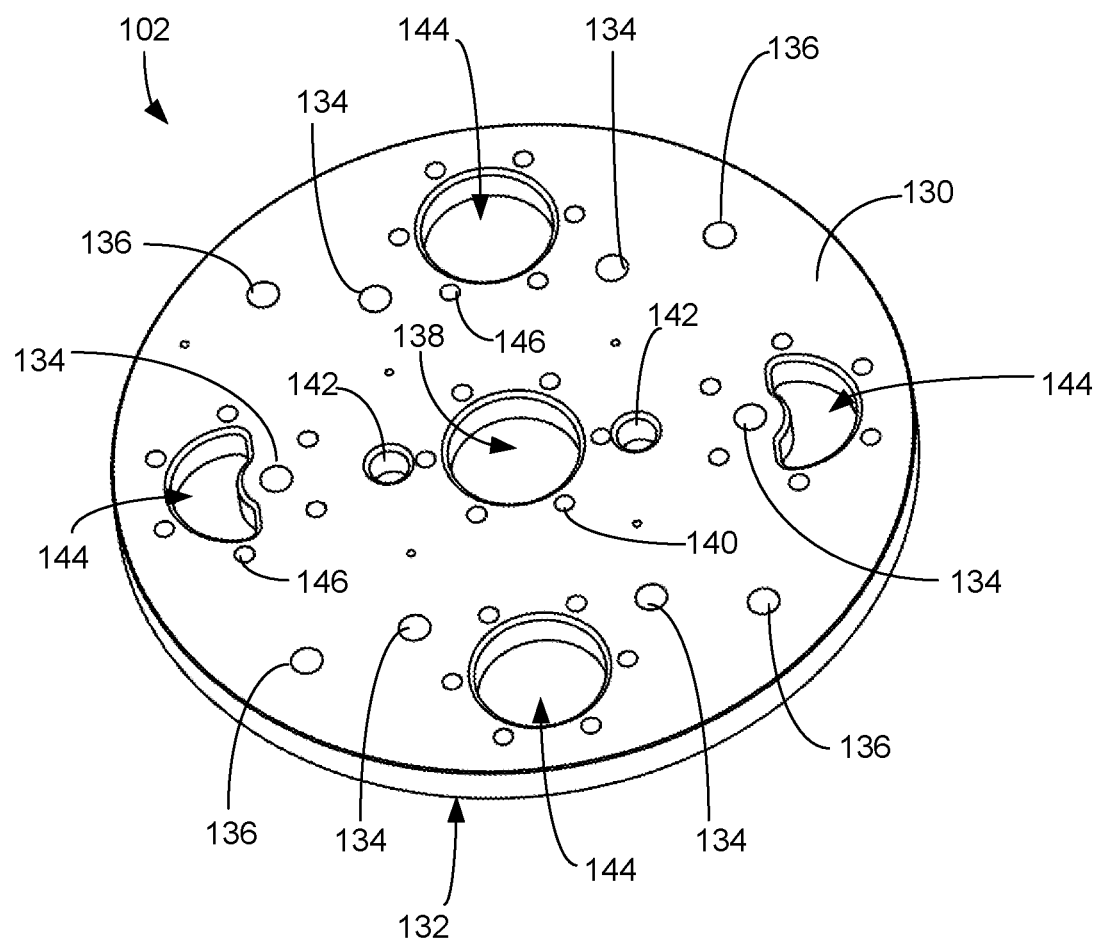
FIG. 3 is a schematic view of an exemplary mounting plate in accordance with an embodiment of the present disclosure.

With additional reference to FIG. 3, the mounting plate 102 includes a first major surface 130 and a second major surface 132 opposite the first major surface 130. The length and width dimensions of each of the major surfaces 130, 132 are greater, typically ten or more times greater, than the thickness of the mounting plate 102. The thickness is the dimension of the mounting plate 102 in a thickness direction orthogonal to the major surfaces 130, 132. As shown in FIG. 2, the thickness direction may be parallel to the longitudinal axis 108.

The mounting plate 102 includes plate mounting orifices arranged in one or more patterns for mounting to the structural plate. In the embodiment shown, one group of plate mounting orifices 134 is arranged in a hexagon pattern and spaced apart from one another in such a manner that the mounting plate may mount to a structural plate having a hexagon mounting pattern. The plate mounting orifices 134 extend through the opposed major surfaces 130, 132 in the thickness direction (along the longitudinal axis 108). Such a hexagon pattern is typically used as a standardized mounting pattern for medical device suspension systems in health treatment settings such as hospital examination rooms, clinics, surgery rooms and emergency rooms. As an alternative to structural plates having a hexagon mounting pattern, some structural plates (e.g., some in the U.S.) have a square (rectangular) mounting pattern. Accordingly, as exemplified in FIG. 3, in some embodiments the mounting plate also includes another group of plate mounting orifices 136 arranged in a square (rectangular) pattern. The plate mounting orifices 136 extend through the opposed major surfaces 130, 132 in the thickness direction (along the longitudinal axis 108). However, it will be understood that in some embodiments, the mounting plate 102 may only include the group of plate mounting orifices 134 arranged in the hexagon pattern; or may only include the group of plate mounting orifices 136 arranged in the rectangular pattern. In still other embodiments, the mounting plate may include a different arrangement of plate mounting orifices for mounting the mounting plate to the structural plate.

The mounting plate 102 includes a primary orifice 138 extending through the opposed major surfaces 130, 132 in the thickness direction (along the longitudinal axis 103). Primary spindle mounting orifices 140 surround the primary orifice and extend through the opposed major surfaces 130, 132 in the thickness direction (along the longitudinal axis 108). As further shown in the exemplary embodiment, in some embodiments, the primary orifice 138 and the primary spindle mounting orifices 140 may also be located adjacent (or between) one or more cable routing orifices 142 extending through the opposed major surfaces 130, 132 of the mounting plate 102.

In some embodiments, the mounting plate 102 includes one or more auxiliary orifices 144 extending through the opposed major surfaces 130, 132 in the thickness direction. Each auxiliary orifice 144 may be surrounded by a respective group of auxiliary spindle mounting orifices 146. The auxiliary spindle mounting orifices 146 extend through the opposed major surfaces 130, 132 in the thickness direction and may be used for mounting an auxiliary spindle to the mounting plate. The exemplary embodiment shown includes four auxiliary orifices. In other embodiments, the mounting plate may include a different number of auxiliary orifices or may not include an auxiliary orifice.

Figure 4:
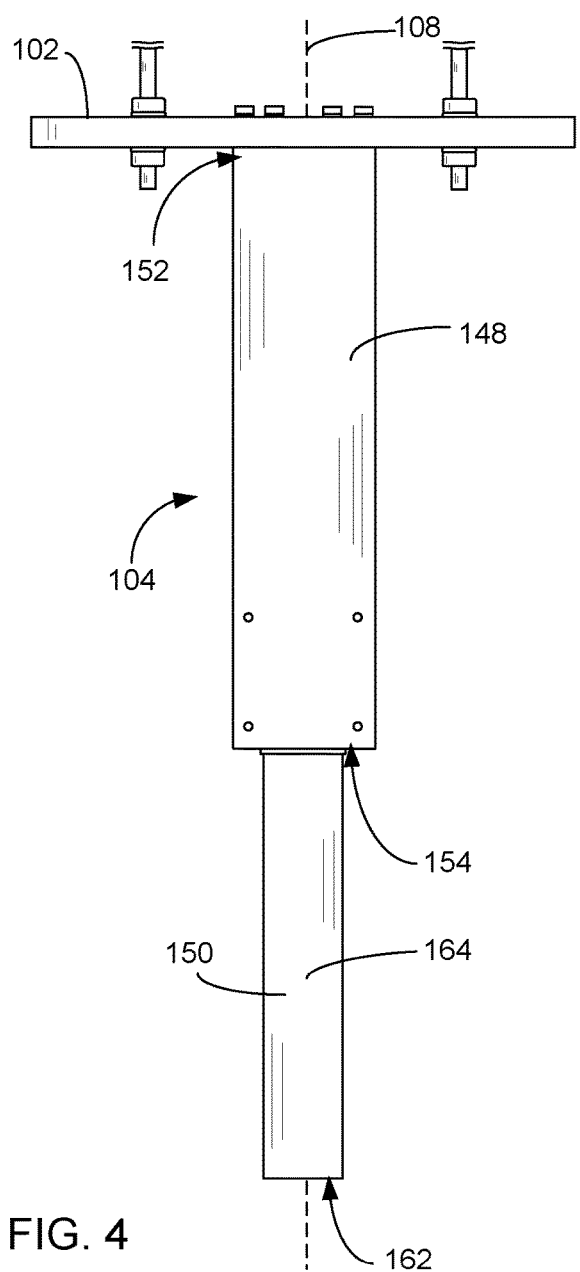
FIG. 4 is a schematic side view of parts of an exemplary medical device suspension system in accordance with an embodiment of the present disclosure.
Figure 5:
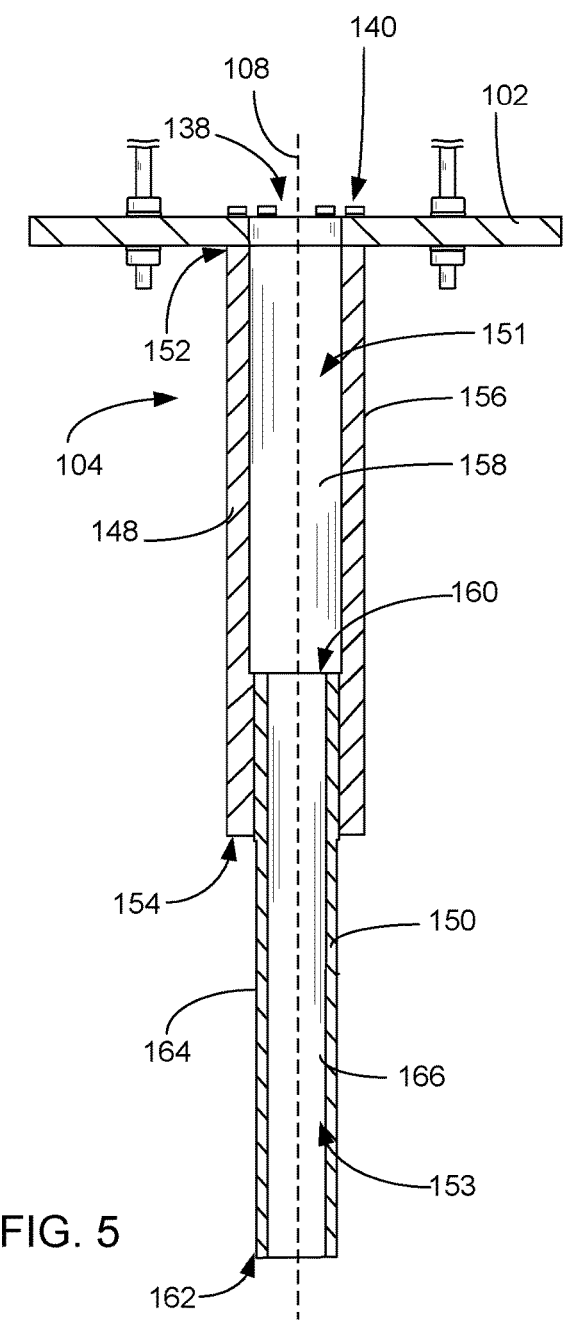
FIG. 5 is a schematic cross-sectional view of parts of an exemplary medical device suspension system in accordance with an embodiment of the present disclosure.

With additional reference to FIGS. 4 and 5, in some embodiments the spindle 104 is formed of two or more parts. Although in other embodiments, the spindle may be a single part. In the embodiment shown, the spindle includes a drop tube portion 148 and a hub mounting portion 150. The drop tube portion 148 extends along the longitudinal axis 108 between a first end 152 and a second end 154 and includes an outer major surface 156. In the embodiment shown, the drop tube portion 148 is a tubular member that also includes an inner major surface 158 that defines an interior volume 151. The diameter of the outer major surface 156 of the drop tube portion as viewed in a plane perpendicular to the longitudinal axis 108 may be any suitable size. In some embodiments, the diameter of the outer major surface 156 of the drop tube portion 148 is 100 mm or more and 150 mm or less. In some embodiments, the diameter of the outer major surface 156 of the drop tube portion 148 is 120 mm. The length of the drop tube portion 148 along the longitudinal axis 108 may be any suitable length, but may be provided with a short length, to thereby provide a low profile of the medical device suspension system (i.e., the overall length of the spindle may be reduced, thereby allowing the length of the device extending from the mounting plate to be minimized). As an example, the length of the drop tube portion 148 (along the longitudinal axis) may be less 350 mm or less. In some embodiments, the length of the drop tube portion 148 (along the longitudinal axis) is 125 mm. In some embodiments, the length of the drop tube portion 148 (along the longitudinal axis) is 150 mm. In other embodiments, the length of the drop tube portion 148 (along the longitudinal axis) is 200 mm. In other embodiments, the length of the drop tube portion 148 (along the longitudinal axis) is 250 mm. In other embodiments, the length of the drop tube portion 148 (along the longitudinal axis) is 330 mm. Of course, in some applications where it is desired/required for the length of the spindle to be longer, the drop tube portion may be longer. For example, in some embodiments, the length of the drop tube portion 148 (along the longitudinal axis) is 505 mm or less. In other embodiments, the length of the drop tube portion 148 (along the longitudinal axis) is 675 mm or less. In other embodiments, the length of the drop tube portion 148 (along the longitudinal axis) is 845 mm or less. In other embodiments, the length of the drop tube portion 148 (along the longitudinal axis) is 1015 mm or less. In other embodiments, the length of the drop tube portion 148 (along the longitudinal axis) is 1185 mm or less. In other embodiments, the length of the drop tube portion 148 (along the longitudinal axis) is 1355 mm or less. In still other embodiments, the length of the drop tube portion 148 (along the longitudinal axis) may be longer than 1355 mm.

The hub mounting portion 150 extends along the longitudinal axis 108 between a first end 160 and a second end 162 and includes an outer major surface 164. In the embodiment shown, the hub mounting portion 150 is a tubular member that also includes an inner major surface 166 that defines an interior volume 153. The drop tube portion and the hub mounting portion are coupled via one or more fasteners (e.g., screws, pins, etc.) and/or adhesive. In the embodiment shown, the outer diameter of the first end 160 of the hub mounting portion 150 fits within the inner diameter of the drop tube portion 148 at the second end 154 of the drop tube portion 148, and the hub mounting portion 150 is mounted to the drop tube portion 148 via fasteners (e.g., screws). The length of the hub mounting portion 150 may be any suitable length. In some embodiments, the length of the hub mounting portion 150 is configured such that it may retain a desired number of hubs. In the embodiment shown, three hubs are mounted to the hub mounting portion 150. In embodiments where the spindle includes the drop tube portion 148 and the hub mounting portion 150, the first end 152 of the drop tube portion 148 may correspond to the proximal end 106 of the spindle and the second end 162 of the hub mounting portion 150 may correspond to the distal end 107 of the spindle.

The spindle 104 is mounted to the mounting plate 102. Respective fasteners (e.g., screws) pass through the primary spindle mounting orifices 140 and are secured to the first end 152 of the drop tube portion 148 of the spindle. The spindle is mounted to mounting plate such that an interior volume 151, 153 of the spindle is in fluid communication with the primary orifice 138. In some embodiments, one or more cables may pass through the primary orifice and into the interior volume 151, 153 of the spindle for routing, for example, the one or more lower extension arms.

Figure 6:
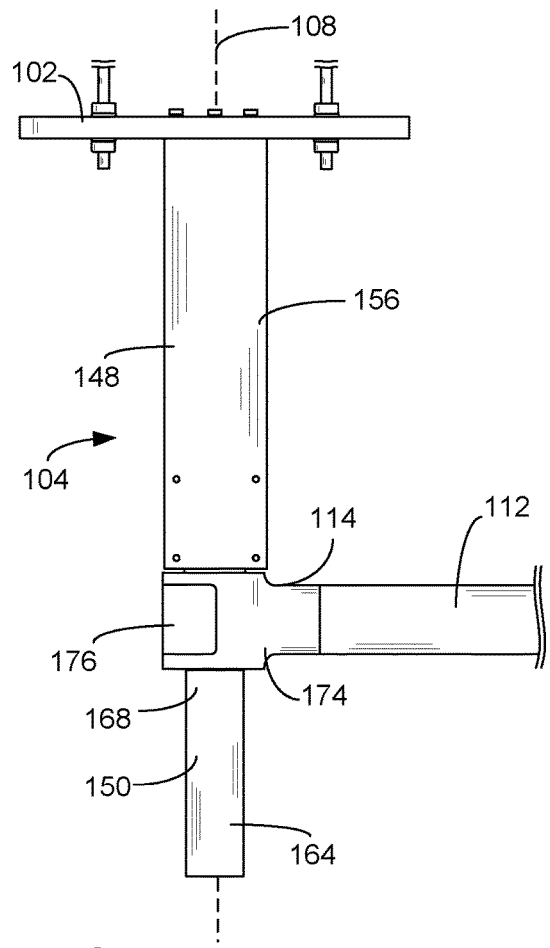
FIG. 6 is a schematic side view of parts of an exemplary medical device suspension system in accordance with an embodiment of the present disclosure.
Figure 7:
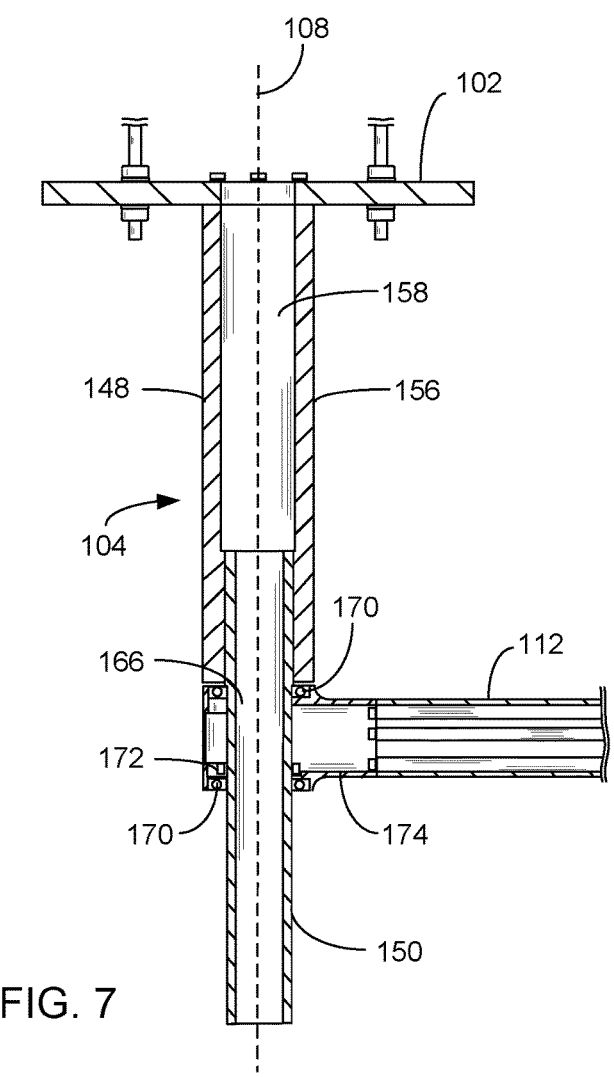
FIG. 7 is a schematic cross-sectional view of parts of an exemplary medical device suspension system in accordance with an embodiment of the present disclosure.

With additional reference to FIGS. 6 and 7, one or more extension arms 112 are mounted to the hub mounting portion 150 of the spindle 104. FIGS. 6 and 7 show the mounting of one extension arm 112. This extension arm is located closest to the drop tube portion 148 of the spindle 104, and may also be referred to as the top extension arm. The top extension arm is mounted to the hub mounting portion 150 of the spindle 104 proximate the second end of the drop tube portion 148 of the spindle 104. Accordingly, the hub associated with the top extension arm may be located approximately the length of the drop tube portion (along the longitudinal axis) away from the mounting plate 102. As shown in FIGS. 1 and 2, additional extension arms may be mounted to the mounting portion of the spindle below the top extension arm. However, as described above, it will be appreciated that in other embodiments, the medical device suspension system may include fewer (e.g., 1, 2) or more (e.g., 4, 5, etc.) extension arms than is shown. Accordingly, in some embodiments, the top extension arm may be the only extension arm.

The hub 114 is mounted to the hub mounting portion 150 of the spindle 104 for rotational movement about the spindle (e.g., about the longitudinal axis). The hub 114 may be mounted on the hub mounting portion 150 of the spindle 104 in any suitable manner. In some embodiments, the hub 114 may be mounted using a spanner nut on the spindle that is used to sandwich the hub bearings of the one or more hubs together, with a retaining ring acting as spacers between hubs. In other embodiments, the hub 114 may be mounted by being fastened via one or more fasteners (e.g., screws) to the spindle. The hub 114 may include one or more bearing assemblies 170 for effecting rotational movement of the extension arm. The hub may also include one or more other features for effecting and/or limiting rotation of the extension arm. For example, in some embodiments, the hub includes a brake assembly 172 for stopping/restricting rotation of the hub 114 and extension arm 112.

One or more stops, such as one or more adjustable stop pin(s) (not shown) may be attached to the spindle 104 to prevent continuous rotation of the extension arm in one or both directions. In other embodiments, the components of the hub 114 (e.g., the bearings or another component) may operate to limitation rotation of the extension arm in one or both directions. The hub 114 may be configured to rotate a predetermined amount about the spindle (e.g., about the longitudinal axis). In some embodiment, the hub 114 is configured to rotate about 360° about the spindle. In other embodiments, the hub is configured to rotate 270° about the spindle. In other embodiments, the hub is configured to rotate about 180° about the spindle.

The components of the hub 114 are disposed in a hub housing 174. The hub housing 174 may also be referred to as a hub cover. The hub housing 174 encloses the bearing assembly 170 (and the brake assembly and stop pins, if included). As shown, in some embodiments, the hub housing may include a removable panel 176, e.g., for access to the components of the hub. In some embodiments, the hub housing 174 may be mounted to a housing 178 of the extension arm 112. In other embodiments, the hub housing and housing of the extension arm may be a single piece. The hub may include a mount for mounting the extension arm thereto.

Figure 8:
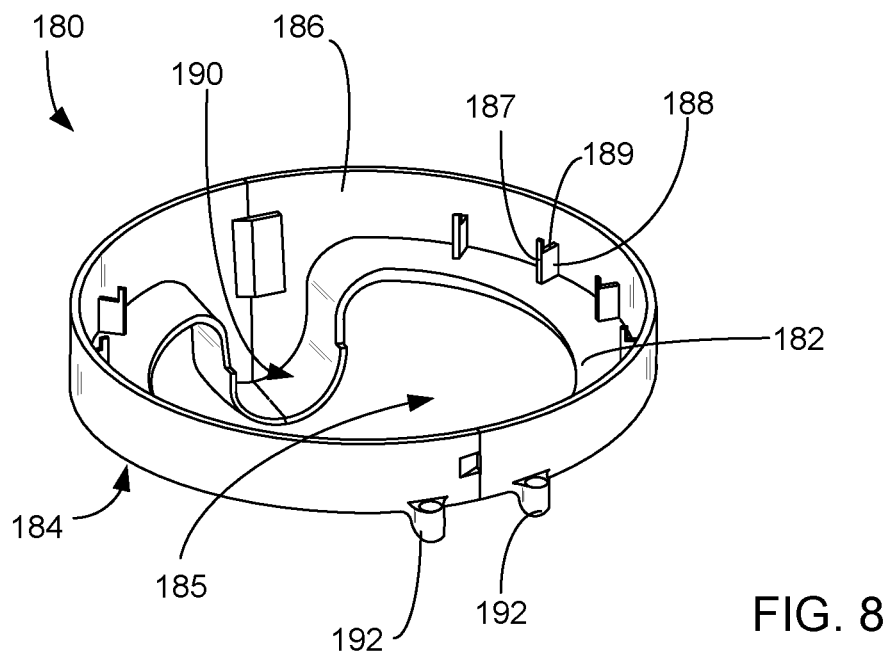
FIGS. 8 and 9 are schematic perspective views of an exemplary top hub cover in accordance with an embodiment of the present disclosure.
Figure 9:
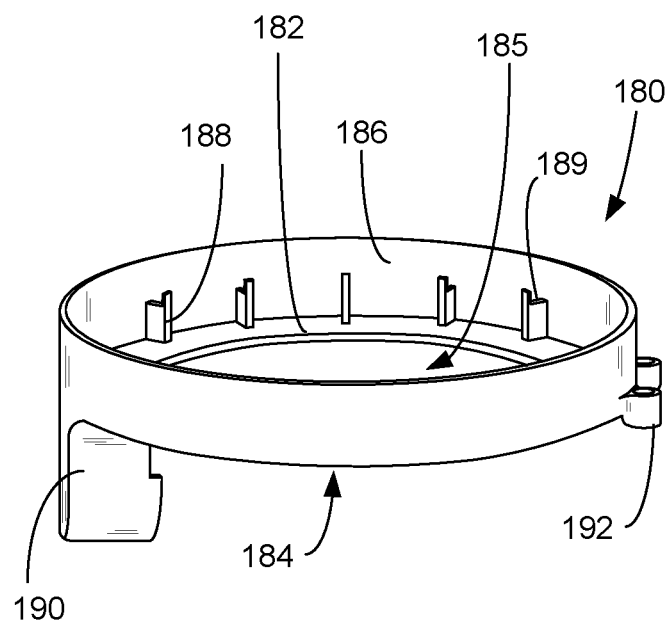

With additional reference to FIGS. 8-10, a top hub cover 180 is provided proximate the second end 154 of the drop tube portion 148 of the spindle 104. The top hub cover 180 is disposed along the longitudinal axis 108 between the hub 114 of the top extension arm 112 and the drop tube portion 148 of the spindle 104 such that the top hub cover 180 is located above the top extension arm.

In the embodiment shown, the top hub cover 180 includes a first major surface 182 and a second major surface 184 opposite the first major surface 182 and spaced apart from the first major surface 182 in a thickness direction. With reference to FIG. 10, the thickness direction may be parallel to the longitudinal axis 108. The major surfaces 182, 184 of the top hub cover are annular in shape as viewed in a plane perpendicular to the longitudinal axis 108. The major surfaces of the top hub cover has an outer circumference and an orifice 185 extends therethrough in the thickness direction. A side wall 186 is proximate the outer circumference of the major surfaces and extends from the first major surface. In the example shown, the side wall 186 extends from the first major surface 182 in a direction parallel to the longitudinal axis 108. With specific reference to FIG. 10, when the top hub cover is oriented on the spindle, the side wall may extend along the longitudinal axis from the first major surface toward the first end of the drop tube. Projections 188 extend from the first major surface in a direction parallel to the longitudinal axis and connect to the side wall. The projections are arranged such that they also extend radially inward from the side wall.

In the exemplary embodiment shown, a portion of the major surfaces are non-planar and form a recessed portion 190 that is offset relative to the remainder of the major surfaces along the longitudinal axis. As described below, the recessed portion 190 may serve as a passage for one or more cables to pass into the hub. In other embodiments, the top hub cover may include another structure instead of the recessed portion that serves as a passage for cable to pass into the hub. Examples include a separate orifice that extends through the major surfaces, a protuberance in the circumference of the orifice, etc. Furthermore, although no specifically shown, in some embodiments the top hub cover may include more than one passage for routing additional cables (e.g., an additional recessed portion, protuberance, and/or orifice).

The hub mounting portion 150 of the spindle 104 may pass through the orifice 185 of the top hub cover 180, and the second end 154 of the drop tube portion 148 of the spindle may abut the first major surface 182 of the top hub cover. The protrusions 188 may be arranged and configured such that end surfaces 187 of the protrusions 188 are proximate and may abut against the outer major surface 156 of the drop tube portion 148 of the spindle.

Figure 12:
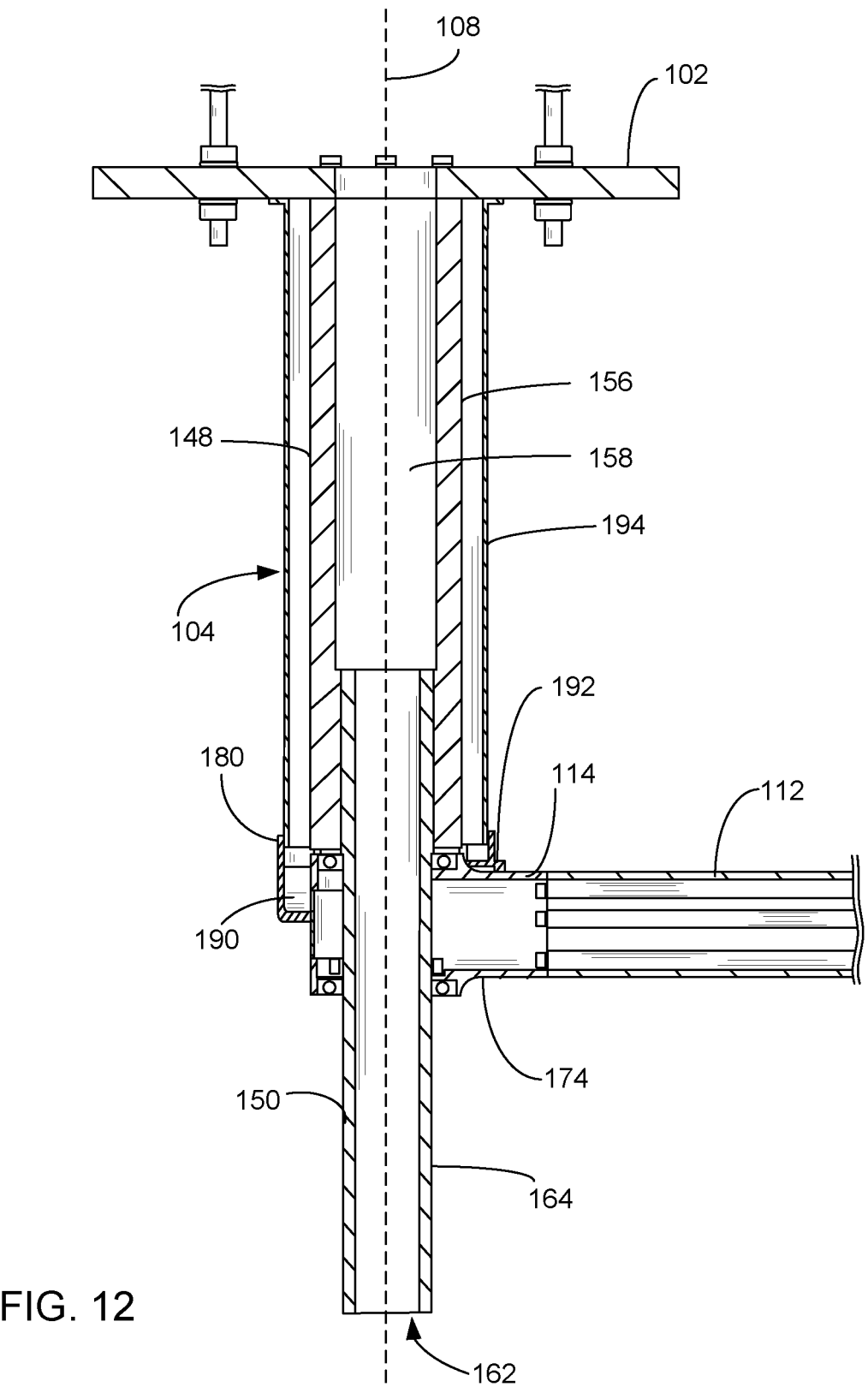
FIG. 12 is a schematic cross-sectional view of parts of an exemplary medical device suspension system in accordance with an embodiment of the present disclosure.

With additional reference to FIGS. 11 and 12, the top hub cover 180 may be mounted to the hub housing 174. In the example shown, the top hub cover 114 includes fastening orifices 192 through which fasteners (e.g., screws) may pass and be fastened to the hub housing. In other embodiments, the top hub cover 114 may be fastened to the housing of the top hub in any other suitable manner (e.g., fasteners, adhesives, etc.). The top hub cover may rotate about the spindle together with housing of the top hub during rotation of the extension arm. Accordingly, rotation of the top hub cover and the hub occurs about the stationary spindle.

As shown in FIGS. 11 and 12, the recessed portion 190 of the top hub cover 180 is adjacent a side of the hub housing 174 of the top hub 114. More specifically, the recessed portion is adjacent the access opening that may be at least partially covered by the access panel 176. The recessed portion (and portion of the side wall 186) of the top hub cover 114 and the access panel 176 may collectively cover the access opening of the hub cover 114. The recessed portion adjacent to the access opening 214 may constitute a passage that provides fluid communication between the gap 200 and the hub housing 174.

The top hub cover may be located approximately the length of the drop tube portion (along the longitudinal axis) away from the mounting plate 102. As an example, in some embodiments, the length of the top hub cover away from the mounting plate (along the longitudinal axis) may be less 350 mm or less. In some embodiments, the length of the top hub cover away from the mounting plate (along the longitudinal axis) may be 125 mm. In some embodiments, the length of the top hub cover away from the mounting plate (along the longitudinal axis) may be 150 mm. In other embodiments, the length of the top hub cover away from the mounting plate (along the longitudinal axis) may be 200 mm. In other embodiments, the length of the top hub cover away from the mounting plate (along the longitudinal axis) may be 250 mm. In other embodiments, the length of the top hub cover away from the mounting plate (along the longitudinal axis) may be 330 mm. In other embodiments, the length of the top hub cover away from the mounting plate (along the longitudinal axis) may be 505 mm or less. In other embodiments, the length of the top hub cover away from the mounting plate (along the longitudinal axis) may be 675 mm or less. In other embodiments, the length of the top hub cover away from the mounting plate (along the longitudinal axis) may be 845 mm or less. In other embodiments, the length of the top hub cover away from the mounting plate (along the longitudinal axis) may be 1015 mm or less. In other embodiments, the length of the top hub cover away from the mounting plate (along the longitudinal axis) may be 1185 mm or less. In other embodiments, the length of the top hub cover away from the mounting plate (along the longitudinal axis) may be 1355 mm or less. In still other embodiments, the length of the top hub cover away from the mounting plate (along the longitudinal axis) may be longer than 1355 mm.

Figure 13:
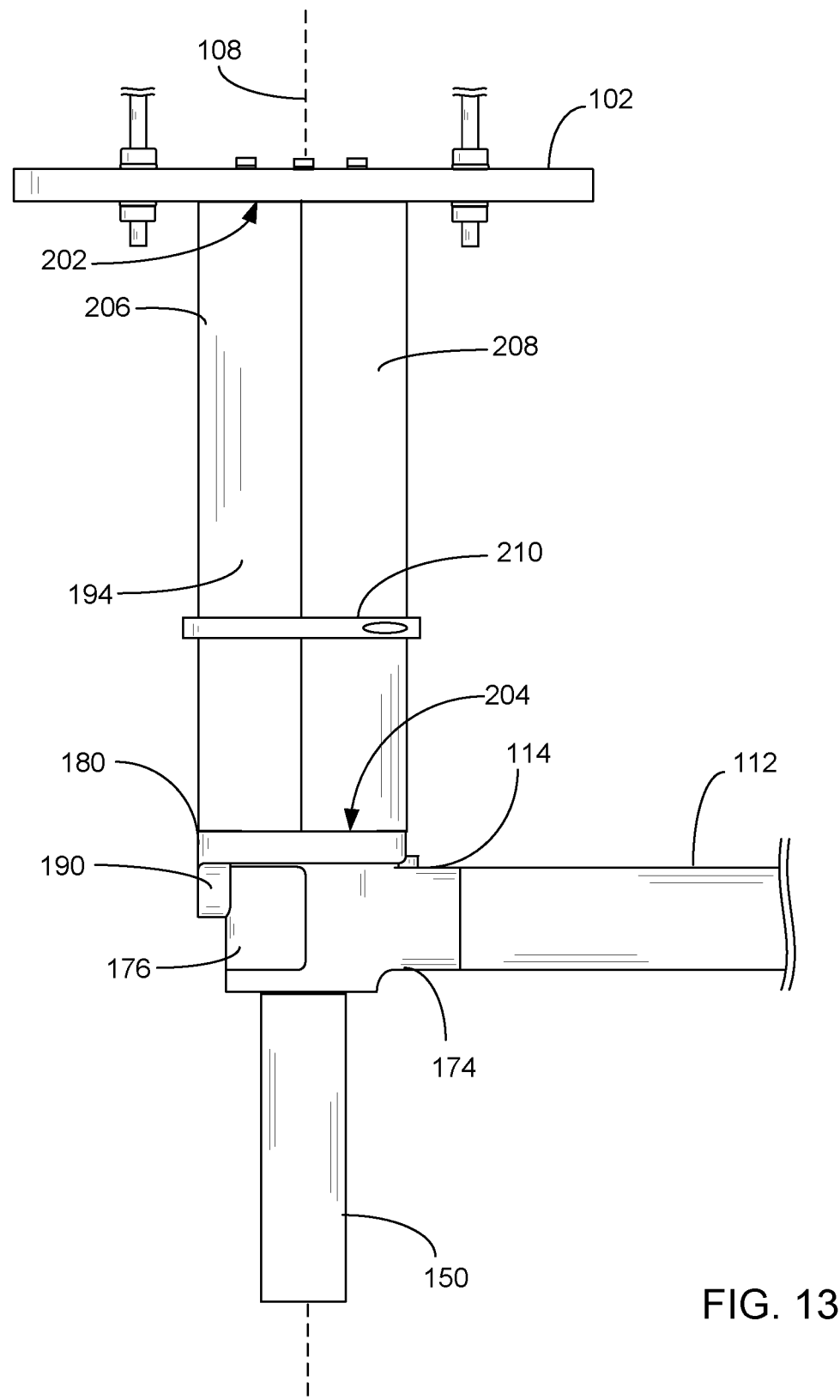
FIG. 13 is a schematic side view of parts of an exemplary medical device suspension system in accordance with an embodiment of the present disclosure.
Figure 14:
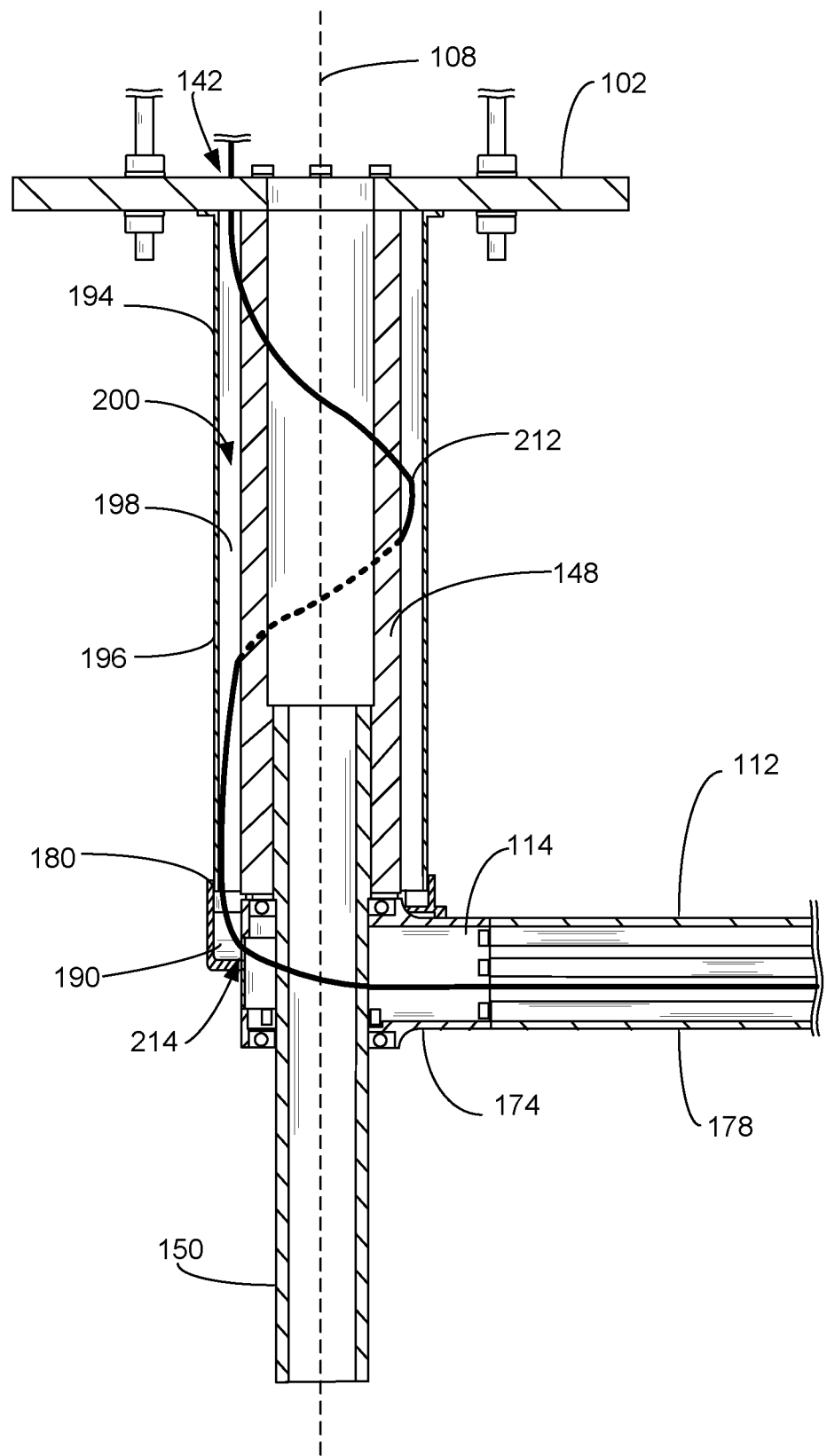
FIG. 14 is a schematic partial cross-sectional view of parts of an exemplary medical device suspension system in accordance with an embodiment of the present disclosure.

With additional reference to FIGS. 13 and 14, a cable management cover 194 surrounds the spindle 104 about the longitudinal axis 108 along a portion of the length of the spindle. The cable management cover 194 extends along the longitudinal axis 108 between the mounting plate 102 and the top hub cover 180. The length of the cable management cover 194 (along the longitudinal axis) may be any suitable length. This length may depend, for example, on the length of the drop tube portion 148 of the spindle 104. The cable management cover 194 is a tubular member that includes an outer major surface 196 and an inner major surface 198. The cable management cover includes a first end 202 proximate the mounting plate and a second end 204 proximate the top hub cover 180.

The inner diameter of the cable management cover 194 is larger than an outer diameter of the drop tube portion 184 of the spindle such that an annular gap 200 is located between the inner diameter of the cable management cover 194 and the outer diameter of the drop tube portion 184. The gap 200 may be provided as any suitable distance between the inner surface of the cable management cover and the outer surface of the drop tube portion. In some embodiments, the gap 200 between the inner diameter of the cable management cover and the outer diameter of the drop tube portion of the spindle in a direction orthogonal the longitudinal axis is 100 mm or less. In other embodiments, the gap 200 between the inner diameter of the cable management cover and the outer diameter of the drop tube portion of the spindle in a direction orthogonal the longitudinal axis is 75 mm or less. In other embodiments, the gap 200 between the inner diameter of the cable management cover and the outer diameter of the drop tube portion of the spindle in a direction orthogonal the longitudinal axis is 50 mm or less. In other embodiments, the gap 200 between the inner diameter of the cable management cover and the outer diameter of the drop tube portion of the spindle in a direction orthogonal the longitudinal axis is 20 mm or less. In other embodiments, the gap 200 between the inner diameter of the cable management cover and the outer diameter of the drop tube portion of the spindle in a direction orthogonal the longitudinal axis is 15 mm or less. In other embodiments, the gap 200 between the inner diameter of the cable management cover and the outer diameter of the drop tube portion of the spindle in a direction orthogonal the longitudinal axis is 10 mm or less. The gap 200 extends along the longitudinal axis 108 between the mounting plate 102 and the top hub cover 180. The second end 204 of the cable management cover 194 sits inside the side wall 186 of the top hub cover. With reference to FIGS. 8 and 9, the second end 204 of the cable management cover 194 may abut the top surfaces 189 of the protrusions 188. The top hub cover 180 may define an end of the gap 200 formed between the inner major surface of the cover and the outer major surface of the spindle along the longitudinal axis 108.

The length of the gap (along the longitudinal axis) may be approximately the length between the mounting plate and the top hub cover (e.g., the length of the drop tube portion (along the longitudinal axis) away from the mounting plate 102). As an example, in some embodiments, the length of the gap (along the longitudinal axis) may be less 350 mm or less. In some embodiments, the length of the gap (along the longitudinal axis) may be 125 mm. In some embodiments, the length of the gap (along the longitudinal axis) may be 150 mm. In other embodiments, the length of the gap (along the longitudinal axis) may be 200 mm. In other embodiments, the length of the gap (along the longitudinal axis) may be 250 mm. In other embodiments, the length of the gap (along the longitudinal axis) may be 330 mm. In other embodiments, the length of the gap (along the longitudinal axis) may be 505 mm or less. In other embodiments, the length of the gap (along the longitudinal axis) may be 675 mm or less. In other embodiments, the length of the gap (along the longitudinal axis) may be 845 mm or less. In other embodiments, the length of the gap (along the longitudinal axis) may be 1015 mm or less. In other embodiments, the length of the gap (along the longitudinal axis) may be 1185 mm or less. In other embodiments, the length of the gap (along the longitudinal axis) may be 1355 mm or less. In still other embodiments, the length of the gap (along the longitudinal axis) may be longer than 1355 mm.

The cable management cover 194 may in some embodiments be fixedly mounted to the mounting plate 102. As an example, the assembly may include a flange 195 (FIG. 15) on the proximal end (proximal the mounting plate) for mounting to the mounting plate. Rotation of the extension arm 112 may result in the top hub cover 180 and hub housing 174 rotating relative to the cable management cover 194 and the spindle 104. In other embodiments, the cable management cover 194 may be fixedly mounted to the top hub cover 174. Accordingly, rotation of the extension arm 112 may result in the cable management cover 194, top hub cover 180, and hub housing 174 rotating relative to the spindle.

In some embodiments, the cable management cover is a two-piece assembly and includes two segments 206, 208. Interlocking fingers (not shown) may be positioned along the length of the cable management cover segments to maintain alignment and attachment of the segments. In some embodiments, a trim ring 210 may be provided at the outer major surface of the cable management cover for retaining the pieces of the cable management cover. In some embodiments where the medical device suspension system includes a canopy (not shown), the trim ring may also retain the canopy.

Figure 15:
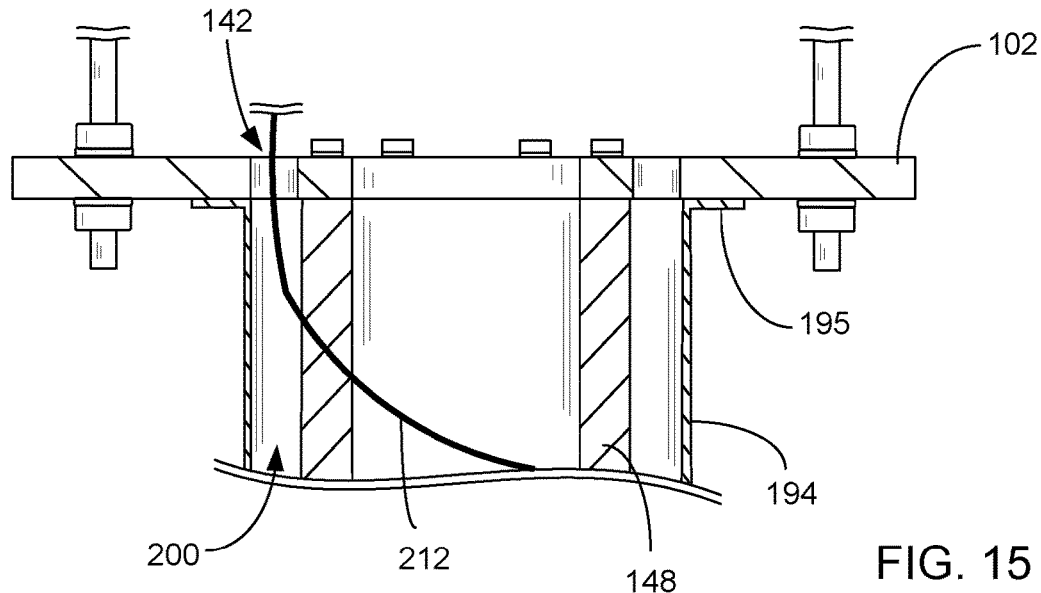
FIGS. 15 and 16 are schematic partial cross-sectional views of parts of an exemplary medical device suspension system in accordance with an embodiment of the present disclosure.
Figure 16:
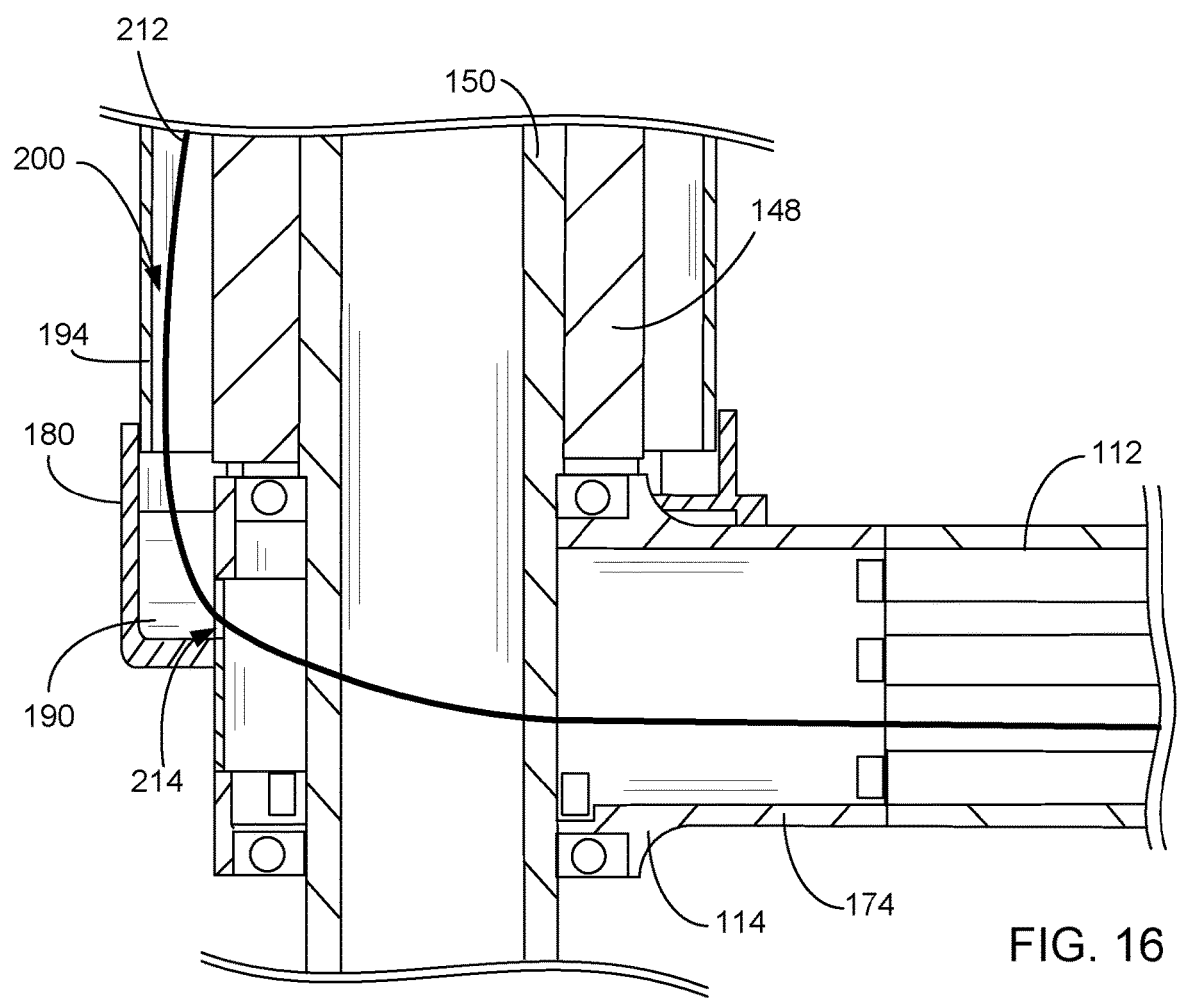

A cable 212 is internally routed through the medical device suspension system from the mounting plate 102 to the extension arm 112. With reference to FIGS. 14-16, a cable routing path is provided through a cable routing orifice 142 of the mounting plate 102, through the gap 200 between the inner surface of the cable management cover and the outer surface of the drop tube portion of the spindle, through the top hub cover, and though the hub housing 174. As shown specifically in FIG. 15, the cable routing orifice(s) is in fluid communication with the gap 200 between the inner major surface of the cable management cover 194 and the outer major surface of the drop tube portion of the spindle. Accordingly, the cable may be routed through the cable routing orifice and into the gap 200 proximate the mounting plate. As shown specifically in FIG. 16, the recessed portion 190 of the top hub cover 180 is adjacent a side of the hub housing 174 of the top hub 114. In the example shown, the recessed portion abuts a portion of the access orifice 214 and provides a passage. Accordingly, the interior of the hub housing is in fluid communication with the gap 200 via the passage. The cable may be routed through the recessed portion of the top hub cover and into the housing of the top hub. The cable may then be routed into the extension arm 112.

It will be understood that FIGS. 14 and 16 show one example of the path in which the gap 200 may be in fluid communication with the interior of the hub housing. As another example, in embodiments where the top hub cover includes a separate orifice that extends through the major surfaces or a protuberance in the circumference of the orifice, this separate orifice or protuberance may provide fluid communication into the hub cover for passage of the cable therethrough.

The cable 212 may constitute a single wire or a bundle of wires. The diameter of the cable is less than the gap between the inner diameter of the cable management cover and the outer diameter of the drop tube portion of the spindle. In some embodiments where the gap between the inner diameter of the cable management cover and the outer diameter of the drop tube portion of the spindle in a direction orthogonal the longitudinal axis is 100 mm, the diameter of the cable is 99 mm or less. In other embodiments where the gap between the inner diameter of the cable management cover and the outer diameter of the drop tube portion of the spindle in a direction orthogonal the longitudinal axis is 75 mm, the diameter of the cable is 74 mm or less. In other embodiments where the gap between the inner diameter of the cable management cover and the outer diameter of the drop tube portion of the spindle in a direction orthogonal the longitudinal axis is 50 mm, the diameter of the cable is 49 mm or less. In other embodiments where the gap between the inner diameter of the cable management cover and the outer diameter of the drop tube portion of the spindle in a direction orthogonal the longitudinal axis is 20 mm, the diameter of the cable is 19 mm or less. In other embodiments where the gap between the inner diameter of the cable management cover and the outer diameter of the drop tube portion of the spindle in a direction orthogonal the longitudinal axis is 15 mm, the diameter of the cable is 14 mm or less. In other embodiments where the gap between the inner diameter of the cable management cover and the outer diameter of the drop tube portion of the spindle in a direction orthogonal the longitudinal axis is 10 mm, the diameter of the cable is 9 mm or less. The difference in size allows for the cable to pass through and move within the gap.

As shown specifically in FIG. 14, the cable 212 enters the gap 200 provided between the cable management cover 194 and the drop tube portion 148 via the cable routing orifice 142 of the mounting plate. The cable 212 is at least partially wrapped around the drop tube portion 148. In the embodiment shown, the cable is wrapped once around the drop tube (i.e., 360°). In other embodiments, the cable may be wrapped more than once around the drop tube (e.g., up to 3 times, or up to 5 times, or up to 10 times). In still other embodiments, the cable may be wrapped less than once around the drop tube portion (e.g., less than) 360°. It is noted that the above-referenced amount of wrapping around the drop tube portion is with respect to the extension arm being in the rotated position in which the cable is wrapped most around the drop tube portion. For example, if the extension arm is limited to 360° of rotation and counterclockwise rotation of the extension arm results in the cable being more wrapped around the drop tube portion, the above-referenced amount of wrapping refers to the amount of wrapping with the extension arm rotated counterclockwise until it is prevented from rotating any further (e.g., by a brake and/or a stop pin). The cable 212 exits the gap 200 and passes through the recessed portion 190 of the top hub cover 180 and into the hub housing 174.

Accordingly, the cable 212 enters the gap 200 proximate the first end of the spindle at a fixed location about the longitudinal axis, and exits the gap through the top hub cover 180. Rotation of the top hub cover 180 about the longitudinal axis 108 causes the position of the recessed portion 190 about the longitudinal axis at which the cable exits the gap to rotate about the longitudinal axis, while the position at which the cable enters the gap about the longitudinal axis remains the same. This rotation causes the wrapped cable to become more or less wrapped around the drop tube, which results in the distance between each rotation to increase or decrease. As an example, as viewed along the longitudinal axis from the proximal end of the drop tube, if the cable 212 is wrapped counterclockwise around the drop tube, rotation of the extension arm in a clockwise direction will cause the cable to become less wrapped around the drop tube and rotation of the extension arm in a counterclockwise direction will cause the cable to become more wrapped around the drop tube.

Because the top hub cover 180 rotates with the hub 114, the amount of wrapping of the cable around the hub mounting portion of the spindle does not vary due to rotation of the extension arm.

In some embodiments, once routed, the cable is retained at the recessed portion 190 from moving further into or out of the hub housing 174 so that the coiling/uncoiling occurs without movement of the cable 114 into and out of the gap. In other embodiments, the cable is not retained in this manner.

It will also be understood that while the figures schematically show a cable (whether it is a single wire or bundle of wires), in other embodiments more than one cable may be routed. Such routing may involve the use of the same or additional cable routing orifices of the mounting plate and use of the same or additional passages of the top hub cover.

The configuration of the medical device suspension system may provide one or more advantages. For example, the configuration may allow for medical devices/accessories requiring cable to be mounted to the top extension arm while maintaining both the desired functionality (e.g., rotatability) of the top extension arm and form factor (e.g., low profile design) of the medical device suspension system. The cable does not need to be externally routed, which would otherwise provide disadvantages in terms of safety/reliability (e.g., risk of tangling/damage of the externally routed wire) and/or aesthetics. The configuration of the medical device suspension system also may eliminate the need for specialized rotation mechanisms that would otherwise limit the type of wire (e.g., brand, thickness, bendability) that can be used to those types of wires compatible with the rotation. The internal routing provided by the configuration of the medical device suspension system may also minimize or eliminate the need to provide external holes in the extension arm, which may maintain its structural integrity.

Physical testing was performed on an automated test fixture to confirm the performance of the design. Cable management covers were provided with both a 15 mm and 20 mm gap relative to the outer major surface of the drop tube portion, respectively, and assemblies including a cable (bundle of wires) routed through the gap were individually tested via an equivalent 10-year life check to test the wires for wear and function. For the 15 mm gap assembly, a cable constituting a bundle of 12 wires was passed through a cable routing orifice of the mounting plate and wrapped once around the drop tube portion of the spindle and routed through the top hub cover and hub. The diameter of the outer major surface of the drop tube portion was 120 mm and the length of the drop tube portion (along the longitudinal axis) was 330 mm. The cable management cover was placed around the cable and drop tube portion, and the wires were tested and found to have a fiber signal of −31.65 dBm and a continuity of 19.7. The assembly was subjected to rotation cycling where the hub was rotated from a position at which the hub was rotated in a counter-clockwise direction until it reached a stop point where it could not rotate any further, and back in the clockwise direction until it reached a stop point where it could not rotate any further (i.e., one cycle) a total of 50,559 times. The hub was configured to rotate about 360° about the spindle. After the rotation cycling, the performance of the cables were again tested and it was confirmed that the wires maintained a fiber signal of −31.65 dBm and a continuity of 19.7.

For the 20 mm gap assembly, a cable constituting a bundle of 12 wires was passed through a cable routing orifice of the mounting plate and wrapped once around the drop tube portion of the spindle and routed through the top hub cover and hub. The diameter of the outer major surface of the drop tube portion was 120 mm and the length of the drop tube portion (along the longitudinal axis) was 330 mm. The cable management cover was placed around the cable and drop tube portion, and the wires were tested and found to have a fiber signal of −31.65 dBm and a continuity of 19.6. The assembly was subjected to rotation cycling where the hub was rotated from a position at which the hub was rotated in a counter-clockwise direction until it reached a stop point where it could not rotate any further, and back in the clockwise direction until it reached a stop point where it could not rotate any further (i.e., one cycle) a total of 73,974 times. The hub was configured to rotate about 360° about the spindle. After the rotation cycling, the performance of the cables were again tested and it was confirmed that the wires maintained a fiber signal of −31.65 dBm and a continuity of 19.6.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device suspension system, including:
a spindle having an outer major surface and extending along a longitudinal axis;
a cable management cover surrounding the spindle about the longitudinal axis and having an inner major surface, the cable management cover extending along the longitudinal axis between a first end and a second end such that a gap is formed between the inner major surface of the cable management cover and a portion of the outer major surface of the spindle;
a hub rotatably mounted to the spindle, the hub including a hub housing;
a top hub cover disposed along the longitudinal axis between the hub and the cable management cover, the top hub cover defining an end of the gap formed between the inner major surface of the cable management cover and the outer major surface of the spindle along the longitudinal axis, the top hub cover comprising a passage in fluid communication with an internal volume of the hub housing, the top hub cover rotatable with respect to the spindle about the longitudinal axis; and
a cable provided within the gap, the cable entering the gap proximate the first end of the cable management cover at a fixed location about the longitudinal axis, the cable passing into the hub housing through the passage of the top hub cover,
wherein rotation of the top hub cover about the longitudinal axis causes the position of the passage to rotate about the longitudinal axis, while the position at which the cable enters the gap about the longitudinal axis remains stationary.

2. The medical device suspension system of claim 1, further comprising a mounting plate, wherein the spindle is mounted to the mounting plate.

3. The medical device suspension system of claim 2, wherein the mounting plate includes cable routing orifice in fluid communication with the gap.

4. The medical device suspension system of claim 2, wherein the cable management cover is mounted to the mounting plate and the top hub cover is rotatable with respect to the cable management cover about the longitudinal axis.

5. The medical device suspension system of claim 1, wherein:
the spindle comprises a drop tube portion and a hub mounting portion;
the drop tube portion extends along the longitudinal axis between a first end and a second end;
the hub mounting portion extends along the longitudinal axis between a first end and a second end;
the first end of the hub mounting portion is mounted to the drop tube portion proximate the second end of the drop tube portion; and
the hub is mounted to the hub mounting portion.

6. The medical device suspension system of claim 5, wherein the length of the drop tube portion along the longitudinal axis is 125 mm to 675 mm.

7. The medical device suspension system of claim 5, wherein the length of the drop tube portion along the longitudinal axis is 150 mm to 330 mm.

8. The medical device suspension system of claim 1, wherein the gap is an annular gap, and the cable is wrapped at least 180° around the spindle.

9. The medical device suspension system of claim 1, wherein the gap is an annular gap, and the cable is wrapped at least 360° around the spindle.

10. The medical device suspension system of claim 1, further comprising an additional hub rotatably mounted to the spindle, the additional hub located further from the top hub cover along the longitudinal axis than the hub.

11. The medical device suspension system of claim 1, wherein the gap between the inner major surface of the cable management cover and the portion of the outer major surface of the spindle is 100 mm or less.

12. The medical device suspension system of claim 1, wherein the top hub cover comprises:
a first major surface and a second major surface opposite the first major surface and spaced apart from the first major surface along the longitudinal axis;
a side wall extending from the first major surface in a direction parallel to the longitudinal axis; and
a recessed portion of the major surfaces that is offset relative to the remainder of the major surfaces along the longitudinal axis, the recessed portion constituting the passage in fluid communication the internal volume of the hub housing.

13. A medical device suspension system, including:
a mounting plate comprising a cable routing orifice;
a spindle mounted to the mounting plate, the spindle having an outer major surface and extending along a longitudinal axis;
a cable management cover surrounding the spindle about the longitudinal axis and having an inner major surface, the cable management cover extending along the longitudinal axis between a first end and a second end such that a gap is formed between the inner major surface of the cable management cover and a portion of the outer major surface of the spindle, the cable routing orifice in fluid communication with the gap;
a hub rotatably mounted to the spindle, the hub including a hub housing; and
a top hub cover disposed along the longitudinal axis between the hub and the cable management cover, the hub cover defining an end of the gap formed between an inner major surface of the cable management cover and an outer major surface of the spindle along the longitudinal axis, the top hub cover comprising a passage in fluid communication with an internal volume of the hub housing, the top hub cover rotatable with respect to the spindle about the longitudinal axis
wherein rotation of the top hub cover about the longitudinal axis causes the position of the passage to rotate about the longitudinal axis, while the position at which a cable enters the gap about the longitudinal axis remains stationary.

14. The medical device suspension system of claim 13, wherein the cable management cover is mounted to the mounting plate and the top hub cover is rotatable with respect to the cable management cover about the longitudinal axis.

15. The medical device suspension system of claim 13, wherein:
the spindle comprises a drop tube portion and a hub mounting portion;
the drop tube portion extends along the longitudinal axis between a first end and a second end;
the hub mounting portion extends along the longitudinal axis between a first end and a second end;

the first end of the hub mounting portion is mounted to the drop tube portion proximate the second end of the drop tube portion; and the hub is mounted to the hub mounting portion.

16. The medical device suspension system of claim 15, wherein the length of the drop tube portion along the longitudinal axis is 125 mm to 675 mm.

17. The medical device suspension system of claim 15, wherein the length of the drop tube portion along the longitudinal axis is 150 mm to 330 mm.

18. The medical device suspension system of claim 13, further comprising an additional hub rotatably mounted to the spindle, the additional hub located further from the top hub cover along the longitudinal axis than the hub.

19. The medical device suspension system of claim 13, wherein the gap between the inner major surface of the cable management cover and the portion of the outer major surface of the spindle is less than 100 mm.

20. The medical device suspension system of claim 13, wherein the top hub cover comprises:

a first major surface and a second major surface opposite the first major surface and spaced apart from the first major surface along the longitudinal axis;

a side wall extending from the first major surface in a direction parallel to the longitudinal axis; and a recessed portion of the major surfaces that is offset relative to the remainder of the major surfaces along the longitudinal axis, the recessed portion constituting the passage in fluid communication the internal volume of the hub housing.

\* \* \* \* \*